US011179216B2

(12) United States Patent
Cohn et al.

(10) Patent No.: US 11,179,216 B2
(45) Date of Patent: Nov. 23, 2021

(54) SYSTEM(S), METHOD(S) AND DEVICE(S) FOR THE PREVENTION OF ESOPHAGEAL FISTULA DURING CATHETER ABLATION

(71) Applicant: Ethicon, Inc., Somerville, NJ (US)

(72) Inventors: William Cohn, Bellaire, TX (US);
Colin Brahmstedt, Houston, TX (US);
Matthew Kuhn, Houston, TX (US);
Fergus Wong, Houston, TX (US)

(73) Assignee: Ethicon, Inc., Somerville, NJ (US)

( * ) Notice: Subject to any disclaimer, the term of this patent is extended or adjusted under 35 U.S.C. 154(b) by 225 days.

(21) Appl. No.: 16/127,461

(22) Filed: Sep. 11, 2018

(65) Prior Publication Data

US 2019/0247139 A1 Aug. 15, 2019

Related U.S. Application Data

(60) Provisional application No. 62/631,359, filed on Feb. 15, 2018.

(51) Int. Cl.
| | |
|---|---|
| *A61B 90/00* | (2016.01) |
| *A61M 13/00* | (2006.01) |
| *A61B 17/34* | (2006.01) |
| *A61B 18/00* | (2006.01) |
| *A61M 25/00* | (2006.01) |
| *A61M 25/04* | (2006.01) |

(Continued)

(52) U.S. Cl.
CPC .......... *A61B 90/04* (2016.02); *A61B 17/3478* (2013.01); *A61B 18/00* (2013.01);
(Continued)

(58) Field of Classification Search
CPC ............ A61B 90/04; A61B 2090/0409; A61B 2090/049; A61B 2090/0427;
(Continued)

(56) References Cited

U.S. PATENT DOCUMENTS 5,380,292 A * 1/1995 Wilson ................. A61M 25/06
604/158
5,423,741 A * 6/1995 Frank .................. A61M 13/003
604/23

(Continued)

FOREIGN PATENT DOCUMENTS

WO WO2015148541 A1 10/2015

OTHER PUBLICATIONS

European Search report for corresponding EPA No. 19157218.9 dated Jul. 25, 2019.

(Continued)

*Primary Examiner* — Nathan R Price
*Assistant Examiner* — Anna E Goldberg-Richmeier (57) ABSTRACT

The present invention is directed to systems, devices and methods for trans-septally delivering carbon dioxide through a minimally invasive catheter to create a gaseous pocket or emphysema between the posterior wall of the left atrium and the esophagus during cardiac ablation of the left atrium. This pocket of gas expanded tissue serves to thermally insulate and separate the esophagus from the left atrium during ablation to prevent the formation of an atrial-esophageal fistula. The system comprises a control system to precisely deliver the gas to a desired location through a needle-based catheter assembly.

9 Claims, 6 Drawing Sheets

(51) Int. Cl.
  *A61B 17/00* (2006.01)
  *A61M 25/02* (2006.01)
  *A61B 18/14* (2006.01)
(52) U.S. Cl.
  CPC ...... *A61M 13/003* (2013.01); *A61M 25/0075* (2013.01); *A61M 25/04* (2013.01); *A61B 18/1492* (2013.01); *A61B 2017/00243* (2013.01); *A61B 2017/00247* (2013.01); *A61B 2017/00292* (2013.01); *A61B 2018/00357* (2013.01); *A61B 2018/00363* (2013.01); *A61B 2018/00577* (2013.01); *A61B 2090/0427* (2016.02); *A61M 2025/0004* (2013.01); *A61M 2025/0091* (2013.01); *A61M 2025/0286* (2013.01); *A61M 2202/0225* (2013.01); *A61M 2205/3334* (2013.01); *A61M 2205/50* (2013.01); *A61M 2210/105* (2013.01)
(58) Field of Classification Search
  CPC ...... A61B 17/3478; A61B 2018/00351; A61B 2018/00357; A61B 17/3474; A61M 13/003; A61M 25/0067; A61M 25/0082; A61M 2025/0002; A61M 2202/0225; A61M 2205/3334; A61N 1/0573
  See application file for complete search history.

(56) References Cited

U.S. PATENT DOCUMENTS

| | | | | |
|---|---|---|---|---|
| 6,258,064 | B1* | 7/2001 | Smith | A61B 17/3478 604/164.12 |
| 7,364,567 | B2* | 4/2008 | Beyerlein | A61B 5/03 604/117 |
| 2003/0191449 | A1* | 10/2003 | Nash | A61B 17/32037 604/523 |
| 2004/0024371 | A1 | 2/2004 | Plicchi | |
| 2006/0253183 | A1* | 11/2006 | Thagalingam | A61B 18/1492 607/120 |
| 2008/0243081 | A1 | 10/2008 | Nance | |
| 2009/0069875 | A1 | 3/2009 | Fishel | |
| 2009/0163862 | A1* | 6/2009 | Kauphusman | A61M 25/0084 604/117 |
| 2010/0168713 | A1 | 7/2010 | Tkebuchava | |
| 2013/0063822 | A1 | 3/2013 | Lin | |
| 2015/0045825 | A1 | 2/2015 | Caplan | |
| 2017/0333122 | A1 | 11/2017 | Rajagopalan | |
| 2017/0360503 | A1 | 12/2017 | Miller | |
| 2018/0361115 | A1* | 12/2018 | Demertzis | A61M 1/0084 |

OTHER PUBLICATIONS

"Anatomic Relations Between the 20 Esophagus and Left Atrium and Relevance for Ablation of Atrial Fibrillation," Circulation 2005; 112:1400-1405.

Kyung Jae Cho, "Carbon Dioxide Angiography: Scientific Principles and Practice", Vascular Specialist International, vol. 31, No. 3, Sep. 2015. https://www.ncbi.nlm.nih.gov/pmc/articles/PMC4603680/.

European Search report for corresponding EPA No. 20157608.9 dated Jul. 27, 2020.

* cited by examiner

SYSTEM(S), METHOD(S) AND DEVICE(S) FOR THE PREVENTION OF ESOPHAGEAL FISTULA DURING CATHETER ABLATION

CROSS-REFERENCE TO RELATED APPLICATIONS

This patent application claims the benefit of U.S. Provisional Application No. 62/631,359 filed Feb. 15, 2018.

BACKGROUND OF THE INVENTION

1. Field of the Invention

The present invention relates to systems, methods and devices for preventing esophageal fistula formation, and more particularly to systems, methods and devices for preventing esophageal fistula formation after intra-cardiac catheter ablation of the left atrium.

2. Discussion of the Related Art

Cardiac arrhythmias, and atrial fibrillation, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Atrial fibrillation affects millions of Americans. Patients with atrial fibrillation have a significantly increased risk of suffering stroke, heart attack, leg loss, and other adverse events. Intra-cardiac catheter ablation has emerged as the dominant therapy for treating atrial fibrillation. By creating full-thickness lines of scar tissue in the left atrium, the chaotic waves of electrical activity necessary to maintain atrial fibrillation are isolated, and the patient's heart rhythm converts to a regular organized one. The lines of scar tissue must be full-thickness, which is to say, must extend from the inner lining of the heart, the endocardium, all the way through the entire thickness of the atrial wall to the outer lining, the epicardium. If the scar tissue is only partial-thickness, the electrical waves can still propagate around the scar.

Biosense Webster is a global leader in the field of treating atrial fibrillation. The Biosense Webster CARTO® 3 system allows accurate mapping of the atrium, navigation inside the atrium with an ablation catheter, and creation of full-thickness lesions. Despite the sophistication of the Biosense Webster system, avoiding occasional post procedural development of an atrial-esophageal fistula remains a challenge. This complication occurs because of the proximity between the esophagus, the swallowing tube that connects the mouth or more accurately, the pharynx to the stomach, and the back wall of the left atrium.

When creating the pattern of left atrial scar that has been identified as most effective in converting atrial fibrillation, it is necessary to create a line that runs transversely across the back wall of the left atrium. During creation of this line, the esophagus may be scarred. This is particularly challenging because usually there is no evidence during the procedure that suggests the esophagus has been injured. The classic presentation is that of a patient who returns two weeks after a "successful" ablation with a low-grade fever of unknown origin or a small stroke. On further investigation, it is revealed that the patient has developed endocarditis, an infection of the heart and heart lining, resulting from drainage of esophageal contents into the heart, or that the patient has had a stroke which resulted from a small bubble of air arising from the esophageal lumen that has passed into the left atrium. Regardless of presentation, the development of an atrial esophageal fistula or abnormal passageway is a potentially serious complication. Patients generally must undergo a major thoracic operation if crisis is to be averted.

Catheter ablation for converting atrial fibrillation to normal organized rhythm requires the successful creation of full-thickness lines of scar tissue in a prescribed pattern throughout the left atrium. One of the lines, by necessity, crosses the back wall where the left atrium and the esophagus are in close proximity. In a significant percentage of cases, the esophagus is inadvertently injured during creation of this burn, which on occasion (0.5 percent to 1.5 percent) results in the delayed formation (approximately two weeks later) of a left atrial-to-esophageal fistula. If the burns do not involve the full thickness of the left atrium wall, the therapy is unlikely to be successful. Electric current may still travel through the partial thickness of living heart muscle and the atrial fibrillation persists. Because of increased awareness of this complication, electrophysiologists less aggressively ablate tissue as they cross the back wall, and fewer patients benefit from successful conversion to regular rhythm as a result. There is consensus among electrophysiologists that a solution is needed to allow aggressive treatment of the left atrium without risk of this potential complication.

Others have proposed solutions. The two main types are: 1) devices that utilize a shaped balloon, rod, or nitinol structure in an effort to pull the esophagus away from the back wall of the left atrium so the electrophysiologist can be more aggressive creating posterior burns; or 2) devices passed down the esophagus that measure temperature, impedance, or other metrics to inform the electrophysiologist when it is safe to burn and when it is not, or when the esophagus is heating up during ablation so the electrophysiologist can stop immediately.

The challenges with the first type include the need for the electrophysiologist to manipulate the esophagus, something with which they typically have little familiarity, and the challenges with moving the esophagus. The two structures, the esophagus and the left atrium, are immediately adjacent to each other in an air-tight space. As one pulls the esophagus away from the left atrium, the atrium is pulled somewhat in conjunction with the esophagus. Moreover, there have been reports of esophageal injury while trying to pull the esophagus by applying traction to it from within its lumen. These injuries include occasional esophageal hematomas, which may require surgical treatment.

The challenges with esophageal temperature monitoring center around its reactive nature. This monitoring only allows the electrophysiologist to determine that the esophagus lumen has increased in temperature, indicating that a thermal insult to the esophageal wall has already occurred. Although this measurement allows the electrophysiologist to immediately stop burning and in so doing, limit the extent of the thermal exposure, the measurement does nothing to prevent such injury from happening.

Accordingly, there exists a need for a reliable system, method and device for preventing esophageal fistula formation during intra-cardiac catheter ablation of the left atrium.

SUMMARY OF THE INVENTION

The present invention is directed to system(s), method(s) and device(s) wherein sufficient volumes of carbon dioxide gas is injected into the layer of connective tissue that sits between the esophagus and the back wall of the left atrium to create a protective layer of insulation that will prevent thermal injury to the esophagus while intentionally creating full-thickness burns in the left atrium. The present invention overcomes a number of the limitations associated with the prior art as briefly described above.

In accordance with one aspect, the present invention is directed to a system for the prevention of an esophageal fistula during intra-cardiac ablation of the left atrium. The system comprising an injection catheter having an elongated body with a proximal end and a distal end, the injection catheter comprising a Tuohy Borst valve, an outer sheath, a hypo tube having a proximal end and a distal end and slidably positioned within the outer sheath, a needle connected to and in fluid communication with the distal end of the hypo tube at the distal end of the injection catheter, and an anchoring device connected to the outer sheath at the distal end of the injection catheter; a gas supply configured to deliver gas to the needle through the hypo tube, the gas supply being connected at the proximal end of the hypo tube; and a feedback control system configured to regulate the pressure and flow rate of the gas from the gas supply to the needle.

Carbon dioxide insufflation, unlike these other approaches, creates an insulating sleeve around the esophagus, in effect isolating the esophagus from the posterior left atrium wall. The reference "Anatomic Relations Between the Esophagus and Left Atrium and Relevance for Ablation of Atrial Fibrillation," Circulation 2005; 112:1400-1405, describes the heterogeneity with respect to the amount and thickness of fibro-fatty tissue interposed between the esophagus and the left atrium. In almost half of the cadavers they dissected, the thickness is less than 5 mm. When carbon dioxide is injected into this fibro-fatty layer, the tissue inflates, and becomes "emphysematous," a term that describes solid tissue infused with gas. The best analogous example from the non-medical world is from foods, such as cotton candy or marshmallows. Each is made from a small volume of sugar that is increased in volume by infusing room or ambient air. Sugar has a density of 1.6 $g/cm^3$ and marshmallow has a density of about 0.4 $g/cm^3$. The volume is increased by a factor of four (4) by infiltrating with air. Similarly, cotton candy has a density of 0.005 $g/cm^3$. It is over ninety-nine (99) percent air. It is also no coincidence that cotton candy looks like the insulation that home builders use when building energy efficient homes. Trapped gas, that is, gas that is not free to blow away with a slight breeze or movement, is an excellent insulator. That explains why Styrofoam® insulates so well (poly-styrene infused with gas), and why fur coats and down feather jackets are so warm. Trapped gas acts as a superb insulator.

In accordance with the present invention, the 3 mm to 6 mm layer of fibro-fatty tissue that separates the posterior left atrium wall from the esophagus will be converted into a thicker layer of gas infused tissue that will surround the esophagus and provide adequate thermal insulation, thereby preventing it from being injured. Carbon dioxide is utilized instead of air to leverage carbon dioxide's water solubility. This has no effect on the ability of carbon dioxide to serve as an insulator as it will behave just like air in this regard, but if carbon dioxide is injected directly into the left atrium, there will be no adverse sequelae. Carbon dioxide is so soluble that it goes readily into solution when pressurized. It makes it highly unlikely to create a carbon dioxide gas embolus, and thereby makes it safe to use inside the left atrium at dosages less than 3 mL/kg. It is important to note that dosages of carbon dioxide less than 3 mL/kg that has been introduced into the cranial circulatory system is tolerated with no neurotoxicity, but the potential to cause embolic stroke in the cranial system does exist. Because a gas is being injected, the needle to be utilized may be small enough, e.g. on the order of a 27-gauge needle, so that the risk of potential injury to the left atrium or esophagus is essentially non-existent.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention is directed to system(s), method(s) and device(s) for preventing or minimizing the formation of an esophageal fistula or esophageal tissue damage due to unintended thermal dispersion during intra-cardiac ablation of the left atrium. In the present invention, carbon dioxide is injected or infused into the fibro-fatty tissue that separates the posterior left atrium wall from the esophagus to expand the tissue and create an insulation layer therebetween. With the carbon dioxide infused tissue insulation layer in place, catheter ablation may be utilized to create full-thickness scar tissue with minimal risk of damaging the esophagus and forming an esophageal fistula. A description of experiments given below demonstrate the feasibility and efficacy of the inventive concept.

An eight-animal study was conducted to demonstrate that carbon dioxide could be safely injected through a catheter inserted up the femoral vein to the right atrium and through the right atrial wall into the pericardium to facilitate obtaining pericardial access. The study demonstrated that carbon dioxide may be safely injected into biological tissue. The study also demonstrated that carbon dioxide offers a number of advantages over air, including high solubility, low viscosity, radio-translucency and excellent thermal and electrical insulation qualities. More specifically, carbon dioxide which is fifty-four times more soluble than nitrogen and twenty-eight times more soluble than oxygen, is typically reabsorbed in less than two hours and is highly unlikely to result in gas embolus, even in large quantities, due to its solubility in water. Carbon dioxide has a low viscosity, allowing it to pass through a needle as small as a 33-gauge needle. The puncture from this size needle seals almost immediately after removal, even in the presence of systemic heparin, thereby reducing the likelihood of complications. Carbon dioxide is also visible under X-ray fluoroscopy, thereby allowing for visible confirmation of successful insufflation by creating an outline of the esophagus under X-ray fluoroscopy. Finally, carbon dioxide is a good electrical and thermal insulator which is exactly what is required to protect the esophagus during intra-cardiac catheter ablation.

The eight-animal study was followed with two separate acute animal experiments. In each, the esophagus of a pig was exposed through a left thoracotomy. Because the esophagus does not run behind the left atrium in pigs, it was possible to directly observe the juxta-esophageal tissue as an indicator of the feasibility of carbon dioxide injection to create a protective barrier layer. A carbon dioxide source was connected to a stopcock which allowed a 60-cc syringe connected to a 27-gauge needle to be filled with pure carbon dioxide. The carbon dioxide was injected into the soft tissue surrounding the esophagus. The carbon dioxide immediately dissected through the soft tissue surrounding the esophagus and increased the thickness of the fibro-fatty layer by creating an emphysema (carbon dioxide infused tissue). The carbon dioxide infused through the tissue all the way around the circumference of the esophagus and tracked toward the head and tail as far as the esophagus was exposed. The thickness of the barrier layer was demonstrated by cutting therethrough. The thickness of the gas-infused tissue was visible on X-ray, presenting as a lucent halo around the esophagus. One may also appreciate that the esophagus moved away from the spine due to the circumferential nature of the carbon dioxide emphysema. Essentially, the carbon dioxide emphysema isolates the esophagus from all other anatomical structures.

Upon completion of the pig studies, two human cadaver studies were conducted to demonstrate the feasibility of forming an insulation layer around the esophagus by creating an emphysema. In both cadavers, a simple investigation was conducted by injecting 120 cc (two complete 60 cc syringes) of carbon dioxide through the back wall of the left atrium. This was also done under direct vision, as the heart in each of the cadavers had been dissected. This study was an endeavor to demonstrate the feasibility of the concept of forming an insulation layer by creating an emphysema or separation. After cutting through the posterior left atrium wall, it was observed that emphysematous tissue between the left atrium and the esophagus formed as it did in the animal studies utilizing carbon dioxide.

The animal experiments were then repeated with additional steps. An esophageal temperature probe was utilized to monitor tissue temperature while intentionally creating lesions on the outer surface of the esophagus using an ablation catheter. Ablation of the esophageal wall was performed both with carbon dioxide insufflation and without carbon dioxide insufflation, to learn of the effects carbon dioxide has on the conduction of thermal energy.

In these evaluations, the esophagus was exposed through a large left thoracotomy. A multi-pole temperature probe was placed through the pig's mouth and down the esophagus under X-ray guidance. The ablation catheter was applied directly to the outer surface of the esophagus and the ablation electrode was aligned with one of the twelve (12) poles of the temperature sensor by X-ray. The ablation catheter was then energized. The measured temperature began to climb almost immediately, from a baseline temperature of 36.6 degrees C., reaching the critical 0.2 degrees C. increase in less than five (5) seconds. With continued energy application, the temperature rose to 40 degrees C. after thirty (30) seconds. The experiment was then repeated under the same conditions, with the only difference being carbon dioxide insufflation was added to the protocol as is explained in greater detail subsequently.

Prior to infusing carbon dioxide to test thermal insulation of the esophagus during ablation, an investigation into how long carbon dioxide would remain in place after injection into the peri-esophageal space was performed. After injecting 120 cc of carbon dioxide into the peri-esophageal fibro-fatty tissue, the tissue would instantly inflate with carbon dioxide, becoming considerably thicker. Yet, the tissue would gradually return to baseline geometry after approximately five (5) minutes. From this simple test it may be reasonably inferred that continuous insufflation with carbon dioxide would be preferable to insuring the insulating layer remained in place when needed during the ablation procedure.

Based on this observation, a 27-gauge needle attached to a long intravenous extension tube was attached directly to the regulator of a small tank of pressurized carbon dioxide. When the needle was inserted into the fibro-fatty tissue around the esophagus, it immediately inflated, as had been previously observed. But the cavity remained inflated until the supply of carbon dioxide was stopped. The rate of carbon dioxide delivery was arbitrarily titrated to be as low as possible with the regulator at hand.

When this experiment was repeated with an ablation catheter and a temperature probe (once again aligning the electrode with the temperature sensor under X-ray) and performing the ablation burn at the same power settings, the temperature readings were significantly different from those observed prior to infusion of carbon dioxide. After thirty (30) seconds of continuous burning, the temperature rose only 0.1 degrees C., from 36.6 degrees C. to 36.7 degrees C., in contrast to the 3.4 degrees C. observed when there was no carbon dioxide present; namely, 36.6 degrees to 40.0 degrees C. Accordingly, carbon dioxide injected into the fatty tissue surrounding the esophagus provided thermal insulation to the esophagus during such a procedure.

Dissection of the peri-esophageal tissue after only 120 cc of carbon dioxide injection or infusion reveals an 8 mm sheath or layer of emphysematous tissue that circumferentially surrounded the esophagus. This tissue is gas infused and conducts radio frequency energy and heat poorly. This 8 mm layer should push the posterior left atrium wall and the esophagus away from each other, thereby allowing aggressive burns to be created across the posterior left atrium wall without fear of esophageal injury.

A system for performing this procedure should preferably be simple for the electrophysiologist to utilize and not interfere with the underlying intra-cardiac catheter ablation procedure. The system should preferably remain in position during the ablation and cause no injury to the left atrium, the esophagus or any biological tissue. The system may also counter the effects of systemic carbon dioxide absorption by utilizing a feedback controller to deliver additional carbon dioxide as needed to maintain the required tissue separation. The system may include a temperature probe. Initially, doctors may place a temperature probe in the esophagus to ensure that the carbon dioxide infused tissue does create a thermal barrier. Once enough evidence exists that proves that the esophagus is thermally insulated, the temperature probe may not be needed. The system may also be utilized just once at the onset of the intra-cardiac catheter ablation procedure to achieve the desired separation between the esophagus and the left atrium and then subsequently removed to allow for the remainder of the ablation procedure, provided the effects of carbon dioxide absorption are negligible.

A system in accordance with the present invention preferably comprises a reversibly deployable needle that advances a short distance from the end of a catheter and locks in that position, but that is in fixed geometric relationship to a sensor that allows its position to be identified on a mapping device such as CARTO® 3, and that has a mechanism for fixing the catheter in place, to prevent it from falling out during ablation. The system also comprises a valve, button, knob or any suitable device that connects the catheter to a small pressurized canister of carbon dioxide with a built-in regulator that: 1) controls the rate and volume of carbon dioxide that can be delivered over the course of the procedure; and 2) for safety, makes it impossible to accidentally hook the device to a gas other than carbon dioxide. The system should also preferably comprise a custom sheath that allows the catheter to be inserted across the atrial septum and locked into position on the posterior left atrium wall, while providing a second lumen for the ablation catheter to be inserted into the left atrium for creation of the burns. Alternative exemplary embodiments are also contemplated as described in greater detail subsequently.

More specifically, an injection catheter for administering carbon dioxide through the left atrium wall as part of the above-described system preferably has certain attributes. The injection catheter should fit through a standard 8.5 French trans-septal sheath and have an integrated stop cock and syringe to allow sterile carbon dioxide to be drawn and delivered. In an alternative exemplary embodiment, the injection catheter may comprise an integral sterile carbon dioxide canister to decrease the setup time and make it easier to utilize. The injection catheter should preferably have the right handling characteristics and column strength to allow the needle to be advanced precisely at the desired point. In one exemplary embodiment, the needle assembly should preferably comprise a 27-gauge needle that only extends to the epicardium to ensure accurate carbon dioxide delivery. In an alternative exemplary embodiment, the 27-gauge needle may extend beyond the epicardium.

In an alternative exemplary embodiment, a catheter with balloons and a deployable needle that is placed through the pharynx and into the esophagus which allows injection of carbon dioxide into these same fibro-fatty tissues through the esophageal wall, in other words "inside out" from the esophageal lumen outward may be utilized. In this alternate exemplary embodiment, the catheter would be similar to the catheter described above.

Figure 1:
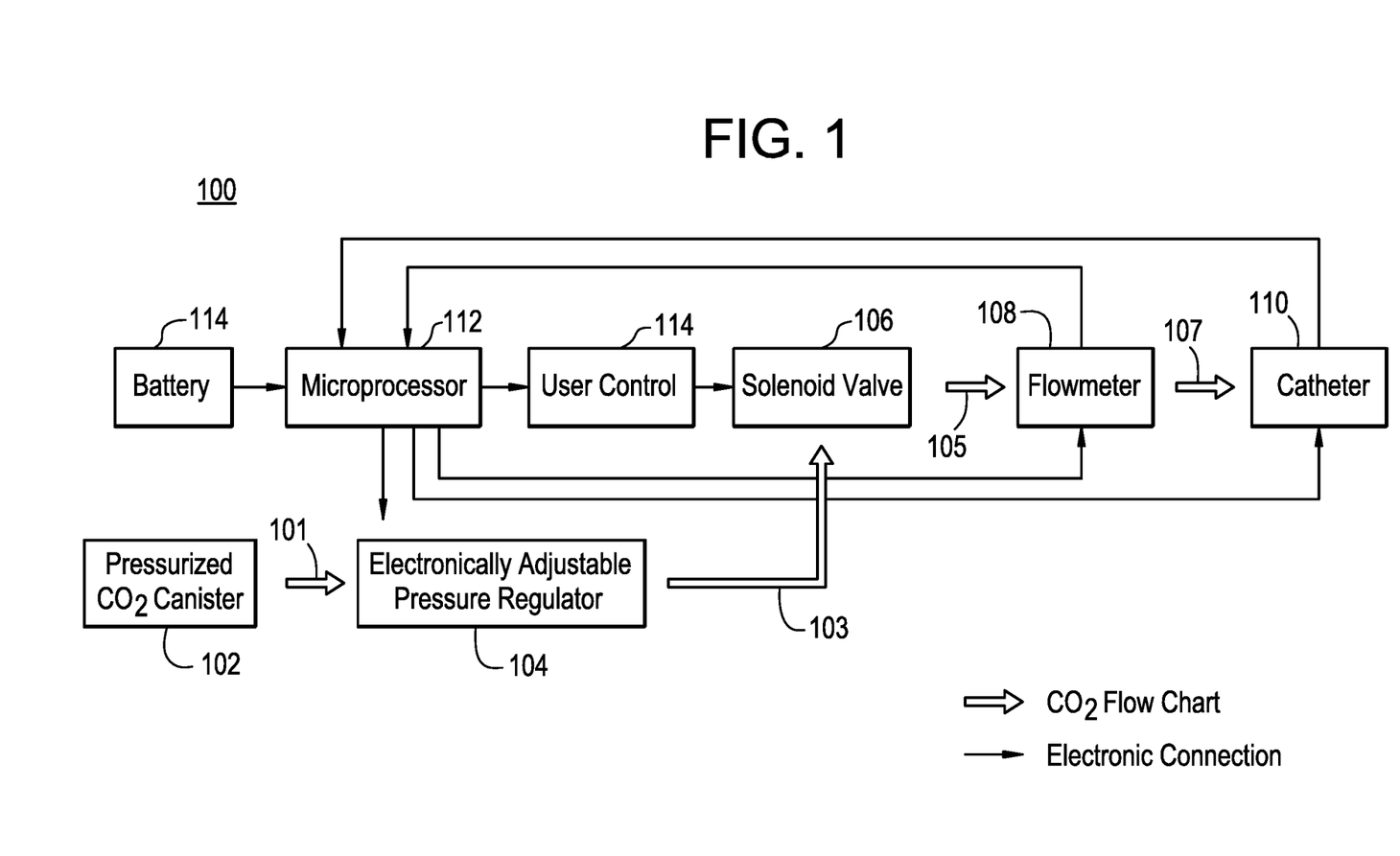
FIG. 1 is a block diagram representation of an exemplary system for the prevention of esophageal fistula during intra-cardiac ablation in accordance with the present invention.

Referring now to FIG. 1, there is illustrated an exemplary embodiment of a system 100 for the prevention of esophageal fistula during intra-cardiac catheter ablation in accordance with the present invention. The system 100 is configured to trans-septally deliver carbon dioxide through a minimally invasive catheter to create a gaseous pocket between the posterior wall of the left atrium and the esophagus. This pocket serves to thermally isolate and separate the esophagus from the left atrium during ablation to prevent the formation of an atrial-esophageal fistula. It is important to note that the system 100 may be implemented utilizing a combination of discrete components, as a unitary, integrated system and/or a combination thereof.

The system 100 is configured as a closed-loop feedback control system and is illustrated in block diagram format for ease of explanation. Carbon dioxide, purified for use in biological applications, is supplied from a pressurized canister 102 and routed through a conduit 101 to a pressure regulator 104. As set forth above, special connectors may be utilized to prevent gas supplies other than carbon dioxide from being utilized. Although illustrated as a single discrete carbon dioxide canister, the gas may be supplied from any suitable source, for example, a central supply. In addition, the pressure regulator 104 may be connected directly to the pressurized canister 102. The pressure regulator 104 is electronically adjustable and is utilized to set and maintain the pressure at which the carbon dioxide is delivered. The operation of the pressure regulator 104 is the same as a pressure regulator on a SCUBA tank or home compressor. A pressure regulator simply maintains the pressure of the gas to be released at a set value for downstream use. The pressure regulator 104 is connected to a solenoid-controlled valve 106 through conduit 103. The solenoid-controlled valve 106 is utilized to control the flow rate of the carbon dioxide from the canister 102 or other supply. The solenoid-controlled valve 106 is connected to a flowmeter 108 via conduit 105. The flowmeter 108 measures the flow rate of the carbon dioxide exiting the solenoid-controlled valve 106 to ensure that it is at the desired flow rate for use in the procedure. The flowmeter 108 is connected to an injection catheter 110 through conduit 107. The injection catheter 110, which comprises a needle assembly described in greater detail subsequently, is utilized to precisely deliver the carbon dioxide to the desired location within the body as described herein. The conduits 101, 103, 105 and 107 may comprise any suitable material that does not react with carbon dioxide, for example, metallic materials such as stainless steel and polymeric materials such as polysiloxanes.

The system 100 also comprises a microprocessor or microcontroller 112. The microprocessor or microcontroller 112 is powered by a power supply 114. The power supply 114 may comprise a battery, either a primary battery or a secondary battery, and/or circuitry for converting power supplied from another source, for example, house power, into a voltage and current level suitable for the microprocessor 112 and other components of the system 100. The microprocessor 112 is programmed to output control signals to the flowmeter 108 and the catheter 110 based upon feedback signals from each as well as preprogrammed control parameters. The microprocessor 112 also outputs control signals to the pressure regulator 104 to adjust the pressure of the gas as required, and to a user control 114. The user control 114 is configured to allow the user of the system 100, for example, a physician or electrophysiologist, to set the parameters of operation via its connection to the solenoid-controlled valve 106 and operates as part of the feed-forward path of the control loop. The microprocessor 112, through its feedback control process automatically adjusts and maintains the operation of the system 100 in accordance with the user's settings. The microprocessor 112 may comprise any suitable processor and associated software and memory to implement the operation of the system 100.

It is important to note that all electronics and electrical connections are protected in a manner suitable for use in an operating or procedure theater. These precautions are necessary to prevent any interaction between an oxygen source and an electrical spark. In addition, all components are preferably manufactured for medical grade usage.

Figure 2:
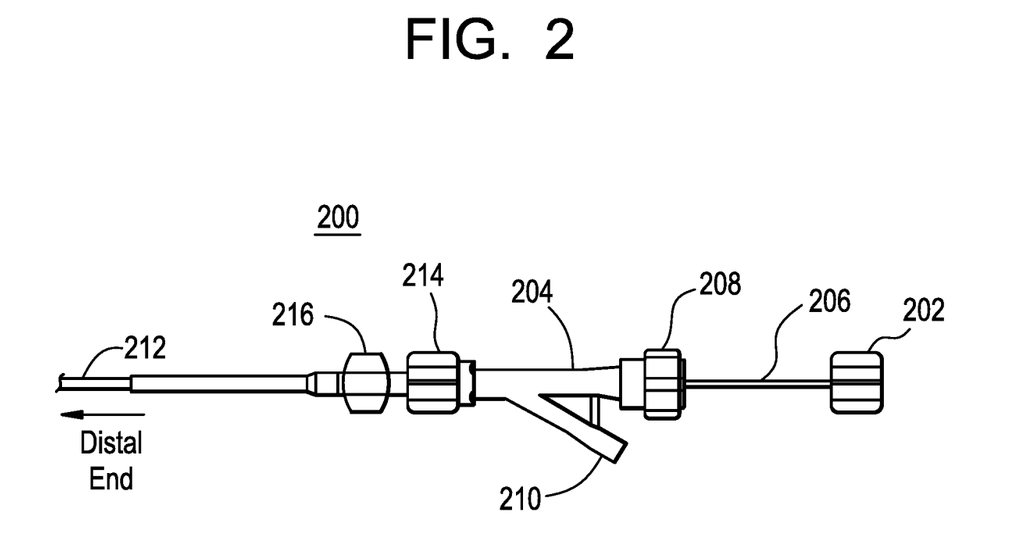
FIG. 2 is a diagrammatic representation of the proximal portion of an exemplary catheter system in accordance with the present invention.

Referring now to FIG. 2, there is illustrated a diagrammatic representation of the proximal region of an exemplary catheter that may be utilized for interventional procedures in accordance with the present invention. The exemplary catheter comprises an elongate body having a proximal end and a distal end. The exemplary catheter 200 comprises a female luer lock connector 202 connected to a Tuohy Borst valve 204 via hypo tube 206 at the proximal valve end 208 of the Tuohy Borst valve 204. The carbon dioxide supply or pressurized canister 102 illustrated in FIG. 1 is connected to the injection catheter 200 via this connection point. As set forth above, unique connectors may be utilized to prevent connection to a different gas supply. In addition, this connection point 202 may be utilized to connect any suitable means for flushing the system. The Tuohy Borst valve 204 also comprises a Y-connection 210. The Y-connection 210 may be utilized to introduce fluids for any number of purposes, including the delivery of contrast agents for fluoroscopic visualization. A proximal shaft 212 is connected on one end to a luer connector 214 of the Tuohy Borst valve 204 via outer shaft luer hub 216 and on the other end to a distal shaft, not illustrated. The Tuohy Borst valve 204, the luer connector 214 and the outer shaft hub 216 are rotationally fixed together to work as a unitary structure. With this configuration, rotation of the Tuohy Borst valve 204 facilitates transmission of torque down the catheter shaft to a fixation coil, as described in detail subsequently, to engage and advance the fixation coil into the heart wall during a procedure. The distal end or region of the exemplary catheter 200 is continuous with the proximal end or region described herein; however, for ease of explanation as it relates to the present invention, the description and drawings are given independently. This basic catheter structure may be utilized for any number of interventional procedures, including the introduction and use of an injection catheter for the delivery of carbon dioxide. A detailed description of the Tuohy Borst valve and the proximal portion of the injection catheter, and the needle assembly or distal portion of the injection catheter of the present invention, as stated above, is given subsequently.

Figure 3:
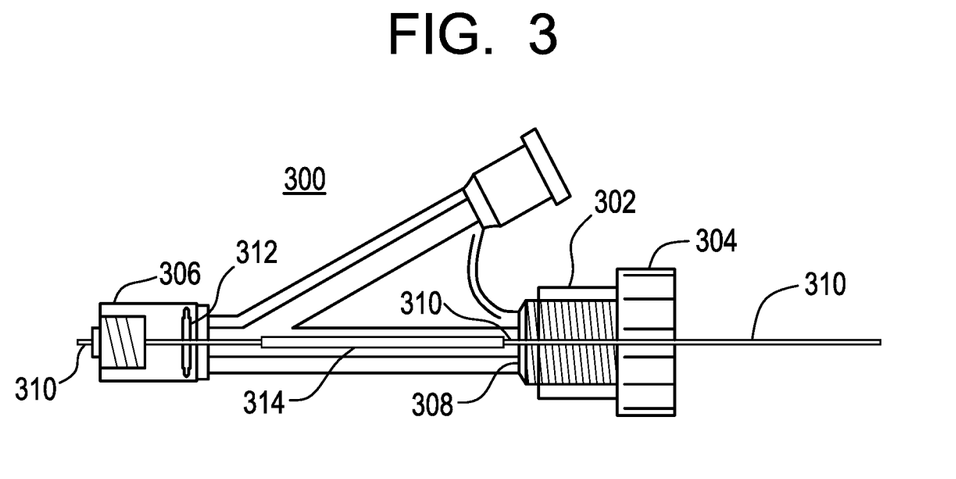
FIG. 3 is a diagrammatic representation of an exemplary Tuohy Borst valve portion of an injection catheter in accordance with the present invention.

FIG. 3 is a diagrammatic representation of a Tuohy Borst valve 300 in accordance with the present invention. The Tuohy Borst valve 300 is essentially the proximal region of the injection catheter in accordance with the present invention. The Tuohy Borst valve 300 comprises a proximal valve 302 with screw lock 304. The proximal valve 302 is threaded to open and close the valve. The screw lock 304 of the proximal valve 302 may be turned clockwise to form a liquid tight seal around any instrumentation, for example, a hypo tube, introduced therethrough to provide a pneumostatic and hemostatic seal. The Tuohy Borst valve 300 also comprises a threaded luer connector 306 which connects the Tuohy Borst valve 300 to the shaft luer hub 216, illustrated in FIG. 2, of the catheter as described briefly above and in greater detail subsequently.

A deformable O-ring 308 is positioned within the proximal valve 302 such that a hypo tube 310 portion of the injection catheter of the present invention passes therethrough. It is through this hypo tube 310 and ultimately a needle attached thereto that the carbon dioxide is introduced into the desired tissue. Referring back to FIG. 1, the hypo tube 310 is part of the catheter block 110. As the screw lock 304 of the proximal valve 302 is tightened (clockwise for right-handed threads), the O-ring 308 is compressed which decreases its inside diameter. This action creates a compressive friction lock on the hypo tube 310 of the injection catheter, which may be utilized to lock the needle in place once the desired tissue depth is achieved. A second O-ring 312 is positioned within the threaded luer connector 306 to create a compressive seal for connection to the shaft luer hub 216, illustrated in FIG. 2. The hypo tube 310 of the present invention comprises a stop mechanism 314. The stop mechanism 314 is a structure mounted around the hypo tube 310 in the region between the O-rings 308 and 312 of the Tuohy Borst valve 300. The diameter or size of the stop mechanism 314 is sufficient to prevent the hypo tube 310 from passing through either non-compressed O-ring 308, 312 to prevent accidental over-deployment of the needle into the target tissue as well as unintentional over-retraction of the injection catheter from the introducer or trans-septal sheath as described in greater detail herein. The hypo tube 310 may comprise any suitable biocompatible material, including any hypo tube materials currently in use in catheters. The stop mechanism 314 may also comprise any suitable biocompatible material. In the exemplary embodiment, the stop mechanism 314 comprises a polymeric material and is bonded to the hypo tube 310 utilizing any suitable means including welding and adhesives.

Figure 4A:
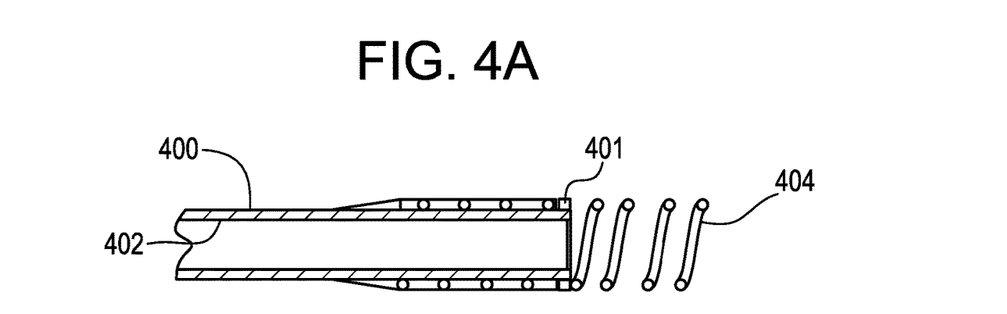
FIGS. 4A-4D are diagrammatic representations of the distal portion of a first exemplary catheter system in accordance with the present invention.

FIGS. 4A-4D are diagrammatic representations of the distal portion of an exemplary injection catheter in accordance with the present invention. FIG. 4A is a sectional or cutaway view of the distal region of an outer sheath 400 of the injection catheter. The outer sheath 400 comprises a tubular structure 402 in which an inner sheath 408 is coaxially positioned. Attached to the distal end of the outer sheath 400 is a fixation coil 404. The fixation coil 404 comprises a corkscrew configuration that functions as a reversible anchoring system to secure the injection catheter in place during carbon dioxide insufflation. The fixation coil 404 is affixed to the outer surface of the distal end of the tubular structure 402 such that a first portion thereof is sealed to the tubular structure 402 and a second portion thereof extends past the end of tubular structure for anchoring in the myocardium. To ensure that the fixation coil 404 and the tubular structure 402 move and operate as a unitary structure, the fixation coil 404 is permanently bonded to the tubular structure 402 by any suitable means. In one exemplary embodiment, a UV curable adhesive is utilized. The tip of the fixation coil 404 comprises a sharp point 406, illustrated in FIG. 4D, to easily pierce the cardiac tissue. The tubular structure 402 may comprise any suitably rigid, biocompatible material that may be navigated through a tortuous vasculature. Standard catheter materials may be utilized. The fixation coil 404 may comprise any suitable rigid biocompatible material that can be twisted into cardiac tissue and anchor therein. Metallic material, for example, stainless steel, or polymeric materials may be utilized. In the exemplary embodiment, the fixation coil comprises stainless steel. The most distal end of the outer sheath 400 also features a radiopaque marker or band 401 for fluoroscopic visualization. The radiopaque marker 401 may be formed from any suitable material, for example, tantalum and bonded to the outer sheath 400 utilizing any suitable means. The radiopaque marker 401 is positioned on the outer surface of the outer sheath 400 and bonded within the inside diameter of the fixation coil 404.

Figure 4B:
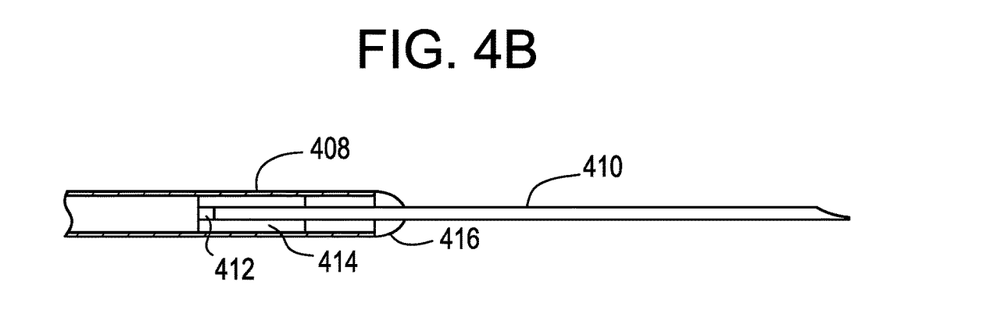

In operation and prior to needle 410, illustrated in FIG. 4B, deployment, the injection catheter is navigated into a position proximate the left atrium such that the fixation coil 404 may be screwed into the myocardium of the left atrium in order to maintain catheter position during carbon dioxide insufflation. Essentially, the fixation coil 404 reversibly anchors the outer sheath 400 to the patient's heart by a simple twisting motion of the injection catheter. As set forth above, twisting or rotation of the Tuohy Borst valve 204, FIG. 2, by the physician facilitates transmission of torque through the outer sheath 400.

FIG. 4B is a sectional or cutaway view of the distal region of the inner sheath 408. The inner sheath 408 comprises a needle 410 that may be advanced through the posterior wall of the left atrium into the juxta-esophageal space or fibro-fatty tissue to deliver a controlled dose of carbon dioxide during an intra-cardiac catheter ablation procedure and then removed. The outer sheath 400 prevents the needle 410 from contacting the surrounding vasculature during navigation of the injection catheter to the target insufflation site. The needle 410 may be retracted back into the outer sheath 400 upon completion of the procedure. The needle 410, which may comprise any suitable material and be sized as set forth herein is connected to the hypo tube 310, illustrated in FIG. 3, via a plastic extrusion 412. In the exemplary embodiment, the needle 410 comprises surgical steel, may comprise any other suitable metallic materials, including nitinol and highly radiopaque materials in alternate embodiments. The connection of the needle 410 to the plastic extrusion 412 and the connection of the plastic extrusion 412 to the hypo tube 310 may be made by any suitable means such that an unobstructed flow of carbon dioxide may be achieved while allowing the three components to act as a unitary structure. In operation, the needle 410 is advanced and retracted by movement of the hypo tube 310 within the outer sheath 400 which is anchored in the myocardium. The needle 410 and the plastic extrusion 412 are coaxially positioned within the lumen of the braided shaft forming the inner sheath 408 inside of a centering element 414. The needle 410 is also slidably sealed to the tip of the inner sheath 408. The centering element 414 and the seal 416 may be made of any suitable biocompatible material.

Figure 4C:
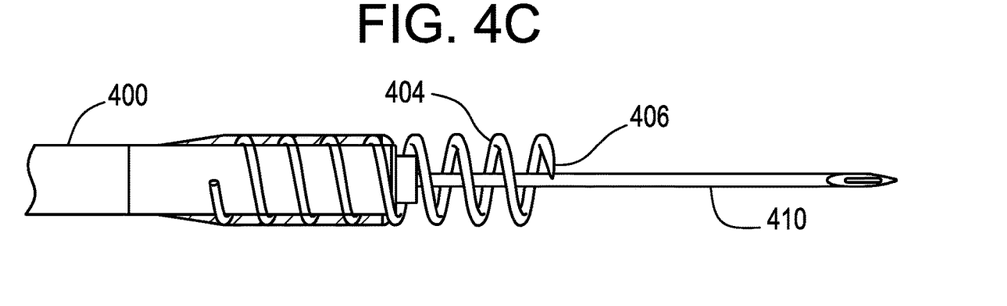
Figure 4D:
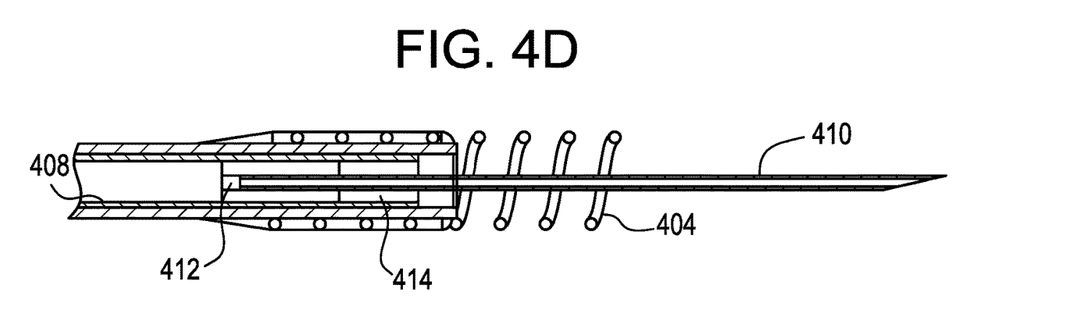

FIG. 4C illustrates the assembled injection catheter distal portion with the inner sheath positioned within the outer sheath 400 and the needle 410 extending therefrom. FIG. 4D illustrates a sectional or cutaway view of the assembled injection catheter distal portion. As explained herein, the injection catheter is navigated through the vasculature and into position proximate the left atrial myocardium. The injection catheter is anchored into position utilizing the fixation coil 404. When properly anchored, the needle 410 is advanced via the hypo tube 310 at the proximal end until the desired tissue depth is reached. Carbon dioxide is then injected into the fibro-fatty tissue that separates the posterior left atrium wall from the esophagus via the exemplary system illustrated in FIG. 1 until the ablation procedure is completed. Upon completion, the fixation coil 404 is removed by twisting the outer sheath 400 in the opposite direction for insertion, and the injection catheter may be removed. The injection catheter does not in any way interfere with the left atrium ablation procedure. In addition, it is important to note that the injection catheter of the present invention may be introduced via the same introducer or trans-septal sheath as the ablation catheter or a completely different one.

Although the distal portion and the proximal portion of the injection catheter is shown in different illustrations for ease of explanation, the two portions form a continuous structure with inner and outer sheaths.

Figure 5:
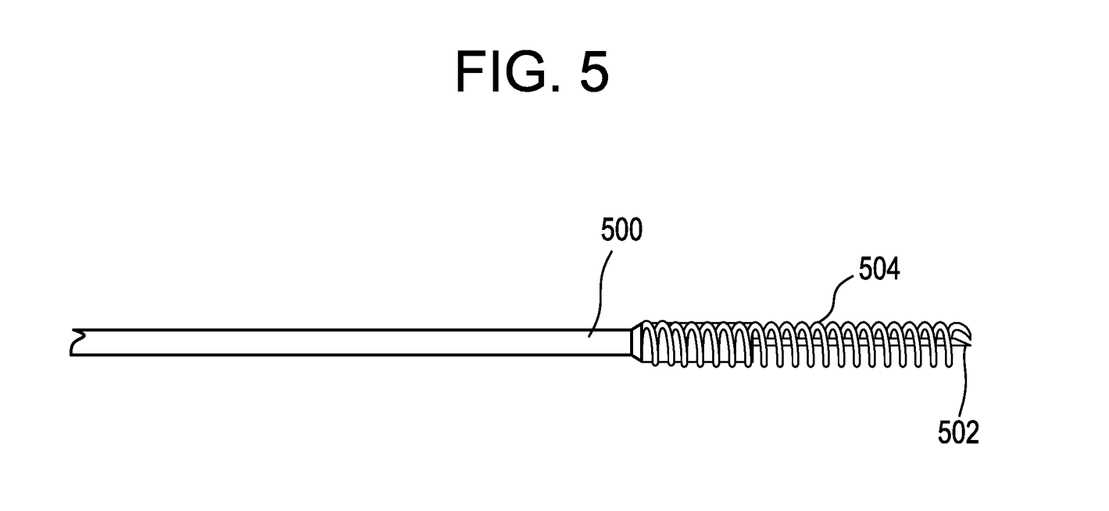
FIG. 5 is a diagrammatic representation of the distal portion of a second exemplary catheter system in accordance with the present invention.

In an alternate exemplary embodiment, the needle may be fixed in place with the fixation coil. Wherein with the exemplary embodiment described above the needle moves independently of the fixation coil by means of the longitudinal movement of the hypo tube, in this alternate exemplary embodiment, the needle remains fixed relative to the coil. In other words, as the fixation coil is twisted into and out of the cardiac tissue, the needle advances or retracts accordingly. FIG. 5 illustrates this alternate exemplary embodiment. As illustrated, the needle 502 is positioned within the fixation coil 504 and both are attached to the end of an outer sheath 500 with the needle 502 in fluid communication as described above.

As set forth above, the needle-tipped catheter or injection catheter is advanced through the posterior wall of the left atrium into the fibro-fatty tissue or juxta-esophageal space to deliver a controlled dose of carbon dioxide to expand the tissue and create an insulation layer during an ablation procedure. In the preferred embodiment, the delivery of carbon dioxide is continuous during ablation rather than through discrete delivery so as to safely maintain tissue expansion. Upon completion of the procedure, the needle may be retracted into the outer sheath of the catheter. In order to precisely deliver the carbon dioxide, the system may employ one or more methodologies to determine the deployment depth of the needle without the need for direct visual confirmation. It is important to note that visual confirmation would be a viable alternative but involve additional complexities.

In one exemplary method, the flow rate of the carbon dioxide exiting the needle may be monitored to determine the resistance to flow. The left atrium space, the myocardial tissue and the fibro-fatty tissue all have different resistivity to gas flow. Accordingly, the physician may simply determine in which tissue layer the needle tip resides by referencing a tissue layer flow rate characterization chart. In an alternative embodiment, the microprocessor 112 (FIG. 1) may be programmed with the flow resistivity of the various tissues or media in the body and receiving feedback from the flowmeter 108 as to the flow rate exiting from the needle, automatically generate an alert via some suitable signal to be displayed or an audible signal that indicates that the proper location for the needle has been achieved. The flowmeter may be utilized to measure the flow resistance at the needle tip and provide feedback directly to the physician or through the microprocessor 112 rather than flowmeter 108.

Figure 6:
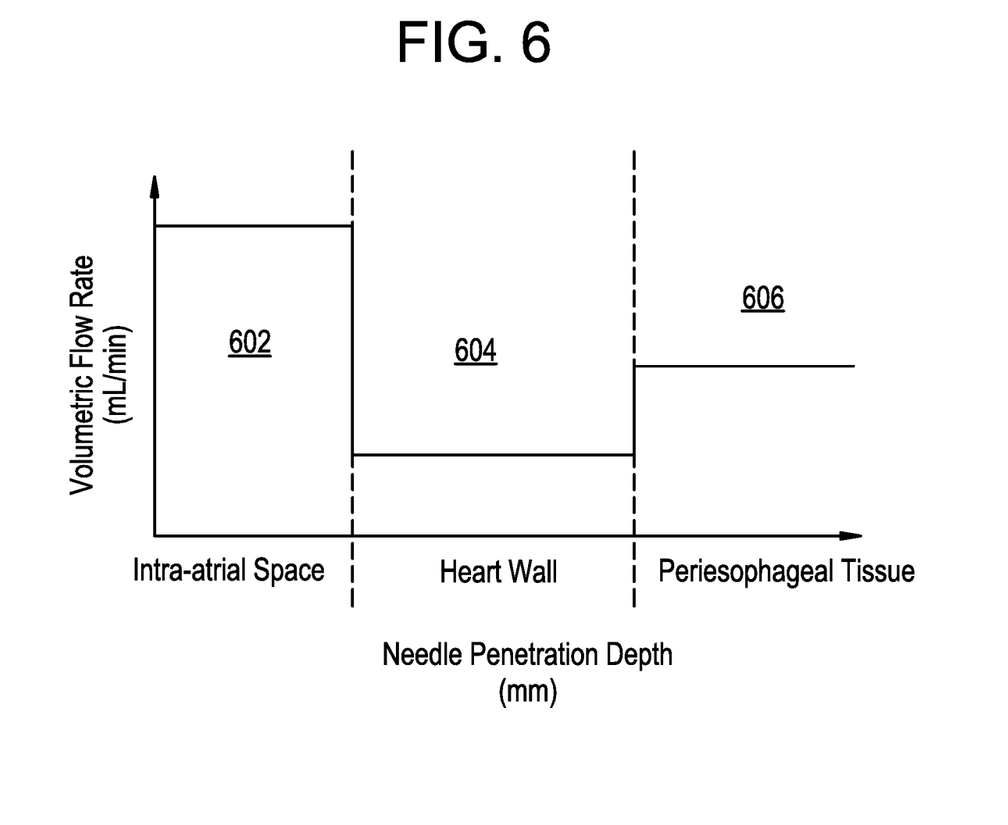
FIG. 6 is a graphical representation of flow rate versus needle penetration depth for various regions of the anatomy in accordance with the present invention.

FIG. 6 is a graphical representation of the relative flow rates of carbon dioxide in the different regions/tissues. The vertical axis represents volumetric flow rate and the horizontal axis represents needle penetration depth in mm. In the first region 602 which represents the intra-atrial space, the flow rate of carbon dioxide is high relative to the other regions as one may expect. In the second region 604 which represents the heart wall, the flow rate of carbon dioxide is significantly lower that the first region 602 given the density of the cardiac tissue. In the third region 606 representing the periesophageal tissue, the flow rate of carbon dioxide is higher than in the heart wall due to lower tissue density but lower than in the intra-atrial space. By measuring flow rate as the needle progresses, one may determine needle location.

In another exemplary method, the electrical activity of the tissue in which the needle is positioned may be monitored. The myocardium has a distinctly different electrical activity profile than the left atrium space and the surrounding tissue. By monitoring this activity with the needle tip, the physician can determine the point at which the needle has contacted and subsequently passed through the myocardium and entered into the fibro-fatty tissue. In this exemplary embodiment, the needle may be configured to provide feedback to a stand-alone sensing circuit or one that is part of the microprocessor. The sensing circuit may be configured to measure the electrical activity, for example, voltage/potential and/or resistance/impedance. As in the previously described embodiment, this information may be routed through the microprocessor 112 which will automatically make the determination or to any suitable device for altering the physician.

Figure 7:
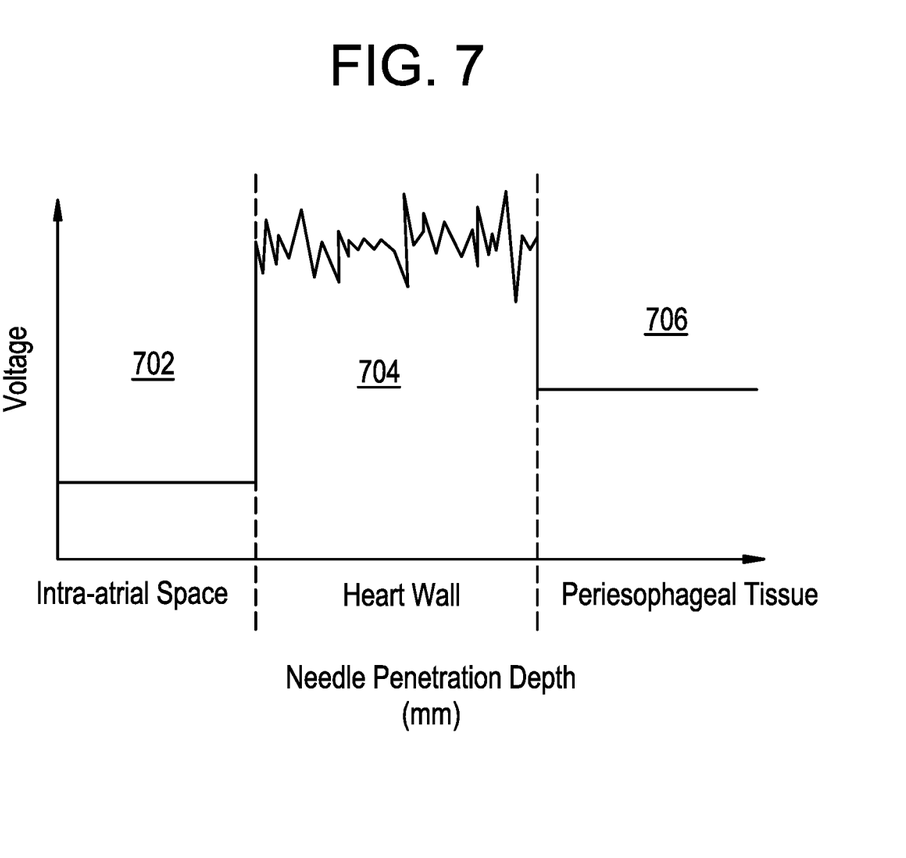
FIG. 7 is a graphical representation of voltage versus needle penetration depth for various regions of the anatomy in accordance with the present invention.

FIG. 7 is a graphical representation of voltage, or potential, vertical axis, versus needle penetration depth, horizontal axis. As illustrated, in the first region 702 corresponding to the intra-atrial space, the voltage sensed by the needle is steady-state and low. In the second region 704 corresponding to the heart wall, the electrical activity is not steady-state and at a higher potential than the first region. In the third region 706 corresponding to the periesophageal tissue, the electrical activity is once again steady-state and of lower potential than the cardiac tissue of the heart wall.

In both exemplary embodiments, real-time monitoring of needle location is achieved without the need for direct visualization.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated but should be constructed to cohere with all modifications that may fall within the scope of the appended claims.

What is claimed is:

1. A system for the prevention of an esophageal fistula during intra-cardiac ablation of the left atrium, the system comprising:
    an injection catheter having an elongated body with a proximal end and a distal end, the injection catheter comprising an outer sheath, a hypo tube having a proximal end and a distal end and slidably positioned within the outer sheath, a needle connected to and in fluid communication with the distal end of the hypo tube at the distal end of the injection catheter, and an anchoring device connected to the outer sheath at the distal end of the injection catheter;
    a gas supply configured to deliver gas to the needle through the hypo tube, the gas supply being connected at the proximal end of the hypo tube, wherein the gas is carbon dioxide; and
    a control system configured to regulate the pressure and flow rate of the gas from the gas supply to the needle, wherein the needle is positionable in the fibro-fatty tissue interposed between the esophagus and the left atrium and wherein the control system maintains a predetermined level of carbon dioxide in the fibro-fatty tissue during intra-cardiac ablation, the control system including an electronically adjustable pressure regulator configured to set and maintain gas pressure, a solenoid valve that controls the rate of flow of gas, a flowmeter to measure the rate of gas flow and a microprocessor, the microprocessor receiving feedback signals from the injection catheter and the flowmeter and outputting control signals to the flowmeter and the injection catheter.

2. The system for the prevention of esophageal fistula during intra-cardiac ablation of the left atrium according to claim 1, wherein the injection catheter further comprises an inner sheath positioned between the outer sheath and the hypo tube.

3. The system for the prevention of esophageal fistula during intra-cardiac ablation of the left atrium according to claim 2, wherein the hypo tube comprises a stop mechanism affixed at its proximal end and configured to prevent over deployment and over retraction of the needle.

4. The system for the prevention of esophageal fistula during intra-cardiac ablation of the left atrium according to claim 3, wherein the hypo tube is configured to slide through the inner sheath for advancing the needle into the fibro-fatty tissue interposed between the esophagus and the left atrium to deliver the gas thereto and to remove the needle when the delivery of the gas is complete.

5. The system for the prevention of esophageal fistula during intra-cardiac ablation of the left atrium according to claim 1, wherein the anchoring device comprises a helical structure with a sharp point, the helical structure is configured to twist into cardiac tissue to secure the injection catheter in position when the outer sheath is twisted.

6. The system for the prevention of esophageal fistula during intra-cardiac ablation of the left atrium according to claim 1, further comprising a means for determining needle position.

7. The system for the prevention of esophageal fistula during intra-cardiac ablation of the left atrium according to claim 6, wherein the means for determining needle position comprises a means for determining the flow rate of gas exiting the needle and a means for comparing the measured flow rates to flow resistivity in various media.

8. The system for the prevention of esophageal fistula during intra-cardiac ablation of the left atrium according to claim 6, wherein the means for determining needle position comprises a means for measuring electric potential at the needle and a means for comparing the measure potential to potential in various media.

9. The system for the prevention of esophageal fistula during intra-cardiac ablation of the left atrium according to claim 6, wherein the means for determining needle position comprises a marker band mounted to the distal end of the outer sheath.

* * * * *